US011022667B2

(12) United States Patent
Ding et al.

(10) Patent No.: US 11,022,667 B2
(45) Date of Patent: Jun. 1, 2021

(54) SYSTEM AND METHOD FOR IMAGE RECONSTRUCTION

(71) Applicant: SHANGHAI UNITED IMAGING HEALTHCARE CO., LTD., Shanghai (CN)

(72) Inventors: Yu Ding, Houston, TX (US); Renjie He, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 580 days.

(21) Appl. No.: 15/638,358

(22) Filed: Jun. 29, 2017

(65) Prior Publication Data

US 2018/0210057 A1  Jul. 26, 2018

Related U.S. Application Data

(63) Continuation of application No. PCT/CN2017/072658, filed on Jan. 25, 2017.

(51) Int. Cl.
*G01R 33/561* (2006.01)
*G06T 5/20* (2006.01)
(Continued)

(52) U.S. Cl.
CPC ........ *G01R 33/5611* (2013.01); *G01R 33/565* (2013.01); *G01R 33/56545* (2013.01);
(Continued)

(58) Field of Classification Search
CPC ... A61B 2576/00; A61B 5/055; A61B 5/7257; G01R 33/5611; G01R 33/565;
(Continued)

(56) References Cited

U.S. PATENT DOCUMENTS 6,841,998 B1    1/2005  Griswold
7,768,264 B1 *  8/2010  Brau ................. G01R 33/5611
                                                    324/307

(Continued)

FOREIGN PATENT DOCUMENTS

CN            103027681 A      4/2013

OTHER PUBLICATIONS

International Search Report in PCT/CN2017/072658 dated Oct. 25, 2017, 4 pages.
(Continued)

*Primary Examiner* — Rishi R Patel
(74) *Attorney, Agent, or Firm* — Metis IP LLC

(57) ABSTRACT

The disclosure relates to a system and method for generating or using a synthesizing filter in image reconstruction. The method may include: acquiring a calibration data set including a plurality of data points, determining a first calibration region in the calibration data set, the first calibration region including a matrix having a plurality of data points, the plurality of data points includes a first data point at the center of the first calibration region, constructing a first relationship between the first data point and the data points in the first calibration region, and generating a synthesizing filter based on the first relationship. The first data point is at the center of the first calibration region. The method may be implemented on at least one machine each of which has at least one processor and storage. The generated synthesizing filter may be stored in the storage in electronic form as a data file. The synthesizing filter may be adapted for determining an unknown data point in an undersampled k-space data set based on a signal acquired by the receiver coil.

20 Claims, 11 Drawing Sheets

(51) Int. Cl.
*A61B 5/055* (2006.01)
*G06T 7/11* (2017.01)
*G01R 33/565* (2006.01)
*A61B 5/00* (2006.01)

(52) U.S. Cl.
CPC ............. *G06T 5/20* (2013.01); *G06T 7/11* (2017.01); *A61B 5/055* (2013.01); *A61B 5/7257* (2013.01); *A61B 2576/00* (2013.01); *G06T 2207/10088* (2013.01)

(58) Field of Classification Search
CPC .... G01R 33/56545; G06T 2207/10088; G06T 5/20; G06T 7/11; G16H 30/40
See application file for complete search history.

(56) References Cited

U.S. PATENT DOCUMENTS

| | | |
|---|---|---|
| 8,379,951 B2 | 2/2013 | Lustig et al. |
| 2008/0279433 A1* | 11/2008 | Brau ................ G06K 9/28 382/131 |
| 2009/0196478 A1* | 8/2009 | Lustig ............. G01R 33/5611 382/131 |
| 2011/0093233 A1 | 4/2011 | Griswold et al. |
| 2013/0300413 A1 | 11/2013 | Hwang et al. |
| 2014/0340083 A1 | 11/2014 | Zhang et al. |
| 2015/0108979 A1 | 4/2015 | Park et al. |
| 2019/0253721 A1 | 8/2019 | Ikeda et al. |

OTHER PUBLICATIONS

Written opinion in PCT/CN2017/072658 dated Oct. 25, 2017, 4 pages.
Mark A. Griswold et al. Generalized Autocalibrating Partially Parallel Acquisitions (GRAPPA). Magnetic Resonance in Medicine, 47(6): 1202-1210, 2002.
Michael Lustig et al. SPIRiT: Iterative Self-consistent Parallel Imaging Reconstruction from Arbitrary k-Space. Magnetic Resonance Medicine, 64(2): 457-471, 2010.
Michael Lustig et al., SPIRiT: Iterative Self-consistent Parallel Imaging. Reconstruction From Arbitrary k-Space, Magnetic Resonance in Medicine, 64:457-471, 2010.
Wang Jinbo, The Optimization Parameters Selection and Weight Adjustment of GRAPPA for Parallel MRI, China Excellent Master's Degree Fulltext Database, 2013, 62 pages.

* cited by examiner

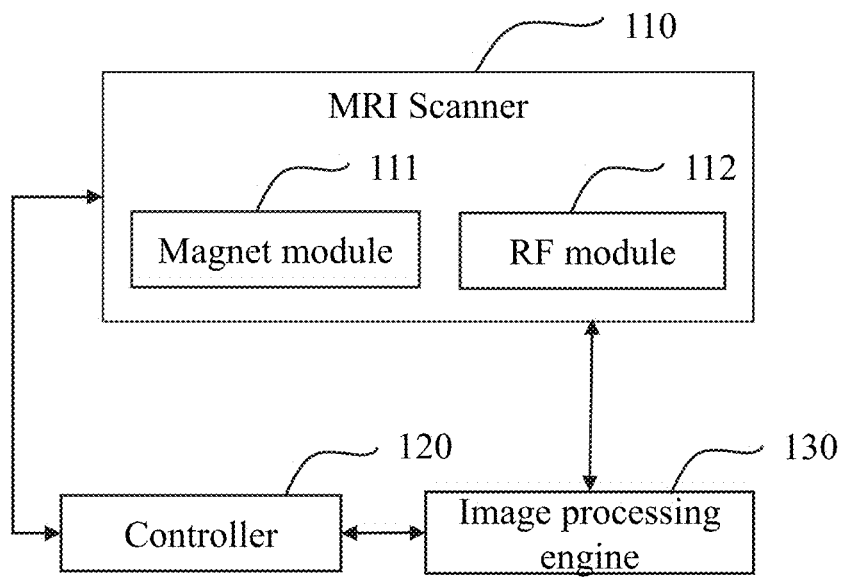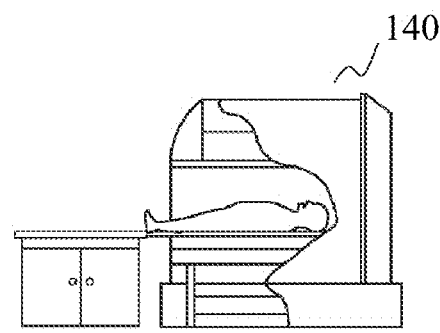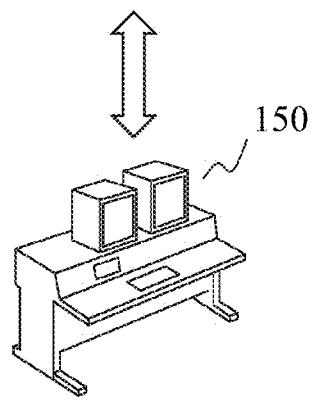
FIG. 1-A

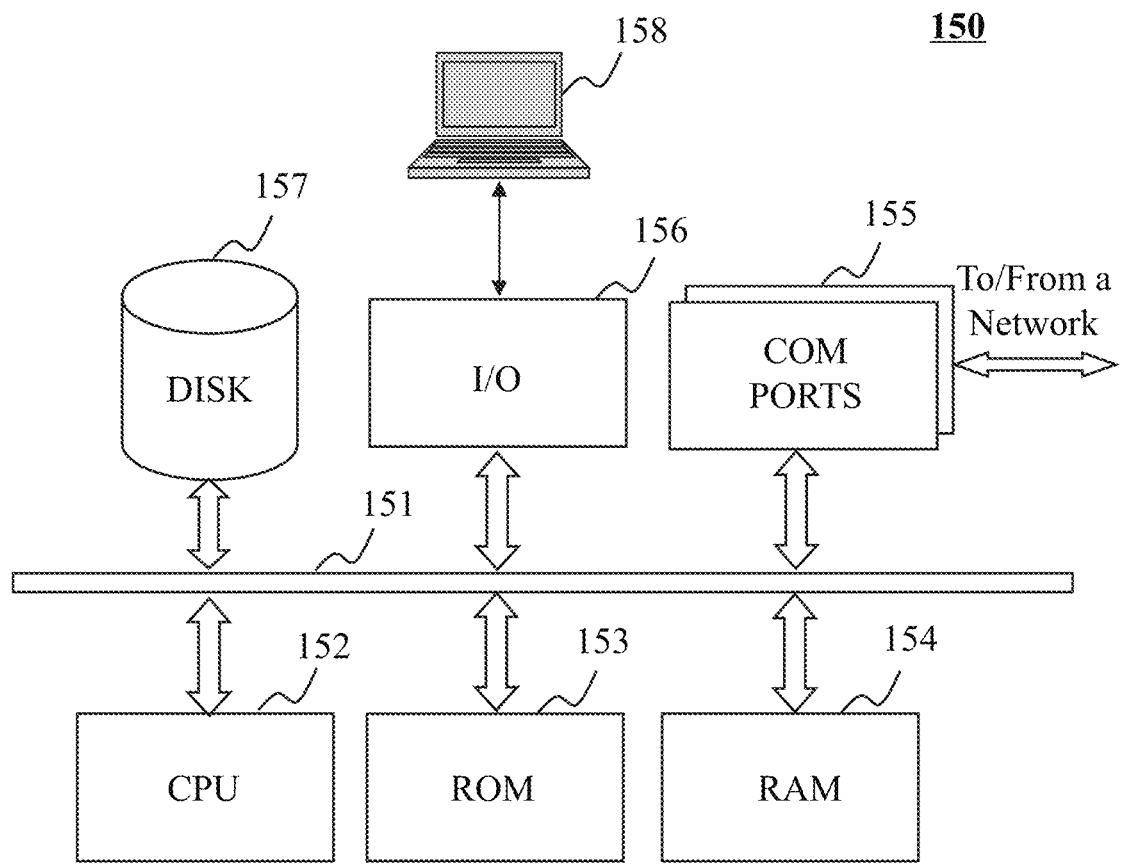
FIG. 1-B

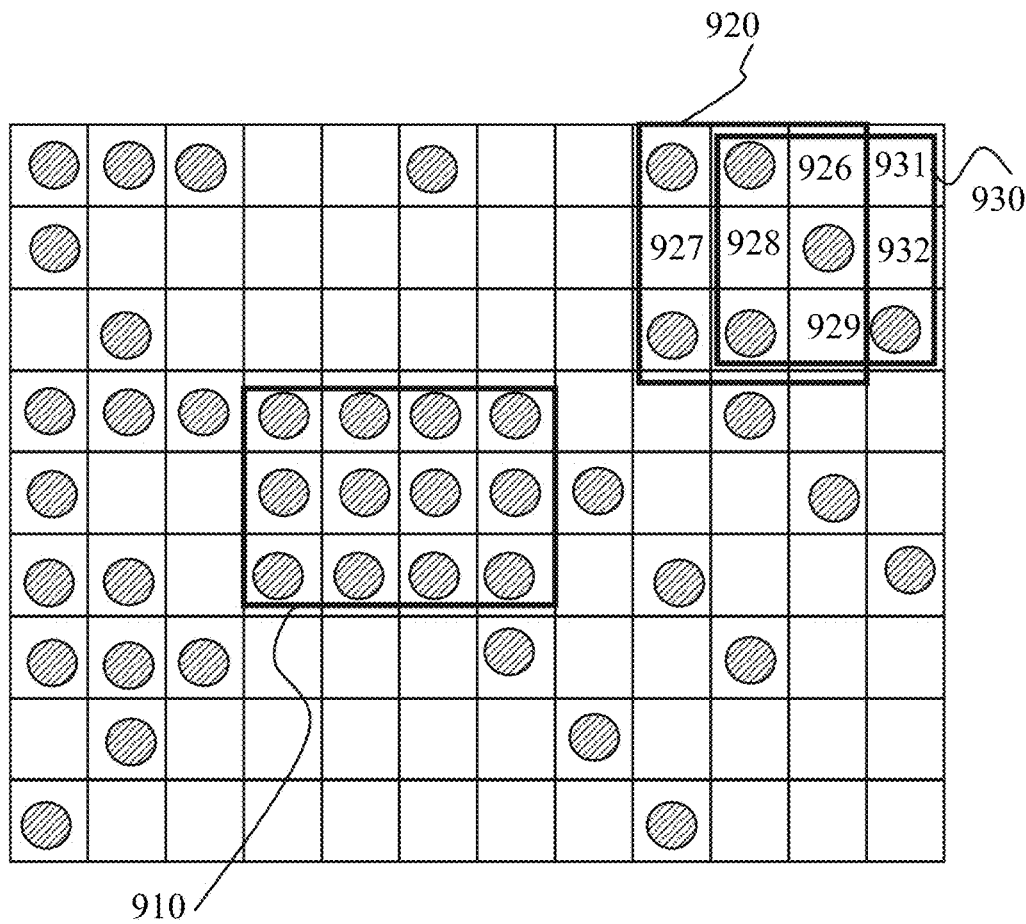
FIG. 9-A
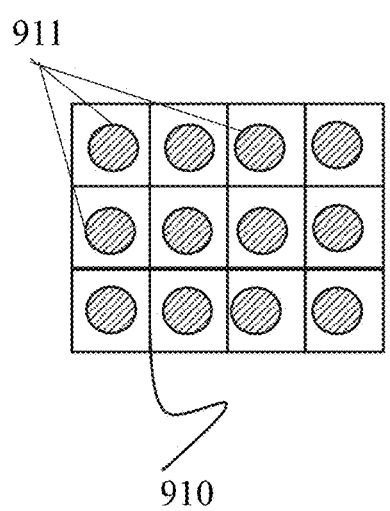
FIG. 9-B
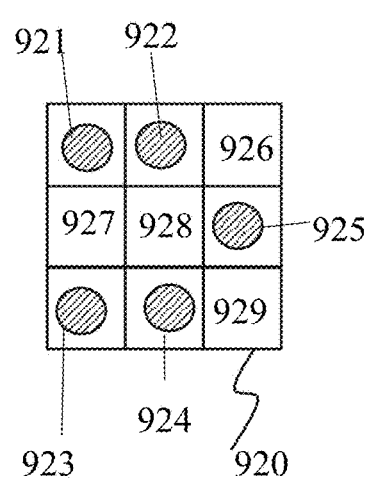
FIG. 9-C
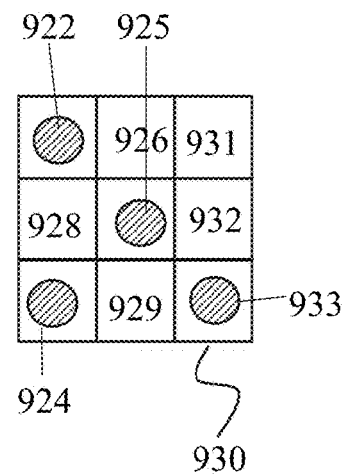
FIG. 9-D

SYSTEM AND METHOD FOR IMAGE RECONSTRUCTION

CROSS-REFERENCE TO RELATED APPLICATION

The present application is a continuation of International Application No. PCT/CN2017/072658, filed on Jan. 25, 2017, the disclosure of which is expressly incorporated herein by reference to its entirety.

TECHNICAL FIELD

The present disclosure generally relates to magnetic resonance imaging (MRI), and more particularly, to a system and method for generating or using a synthesizing filter in image reconstruction.

BACKGROUND

Magnetic resonance imaging (MM) is a widely used medical technique which produces images of a region of interest (ROI) by exploiting a powerful magnetic field and radio frequency (RF) techniques. During an MRI process, the acquired signals may be processed and filled into the k-space, and then data in the k-space may be transformed to reconstruct MRI images. Parallel imaging uses multiple receiver coils that each may receive signals from a subset of the total volume and combines data of the multiple receiver coils to provide an image for the total volume. In some embodiments, parallel imaging techniques exploit the sensitivity of the receiver coils to accelerate MM signal acquisition. However, the application of a current parallel imaging technique may include a user intervention. For instance, a user (for example, a doctor, a nurse, etc.) may need to provide a parameter for the application of a parallel imaging technique. There is a need to provide a system and method for executing parallel imaging automatically and conveniently.

SUMMARY

In a first aspect of the present disclosure, a method for generating a magnetic resonance (MR) image is provided. The method may include one or more of the following operations. A plurality of MR signals may be acquired by a receiver coil. The receiver coil may include a body coil and/or a surface coil. A calibration data set relating to the plurality of MR signals may be acquired. The calibration data set may include a fully-acquired k-space data set that includes no unknown data points. In some embodiments, the calibration data set may be generated based on complete signals and/or undersampled signals. A first calibration region in the calibration data set may be determined. The calibration region may be part of the calibration data set. The calibration region may have a size of n×m, wherein n or m may each represent an integer. The first calibration region includes a matrix having a first plurality of data points, the first plurality of data points includes a first data point at the center of the first calibration region. A first relationship between the first data point and the first plurality of data points including the first data point in the first calibration region may be constructed. A synthesizing filter may be generated based on the first relationship. The synthesizing filter may be stored in electronic form as a data file. The synthesizing filter may be adapted for determining an unknown data point in an undersampled k-space data set based on a signal acquired by the receiver coil. In some embodiments, the synthesizing filter may be a convolution kernel. In some embodiments, the convolution kernel may be of the same size as the first calibration region.

In some embodiments, the method may further include one or more of the following operations. A second calibration region in the calibration data set may be determined based on the first calibration region. The second calibration region may have the same size as the first calibration region. In some embodiments, the second calibration region and the first calibration region may be in the same k-space lines. The second calibration region may include a matrix having a second plurality of data points, the second plurality of data points includes a second data point at the center of the second calibration region. A second relationship between the second data point and the second plurality of data points including the second data point in the second calibration region may be constructed. The synthesizing filter may be generated based on the first relationship and the second relationship.

In some embodiments, the convolution kernel may be of the same size as the first calibration region and the second calibration region. The synthesizing filter may be arranged according to a Cartesian sampling pattern. The synthesizing filter may be arranged according to a non-Cartesian sampling pattern. Exemplary non-Cartesian pattern may include but not limited to radial and spiral pattern. In some embodiments, the non-Cartesian pattern may be gridded to a Cartesian coordinates.

In some embodiments, the signal acquired by the receiver coil may represent the undersampled k-space data set. The synthesizing filter may be applied on the undersampled k-space data set to form a complete k-space data set in which the unknown data point in the undersampled k-space data is determined. An image data set may be generated based on the complete k-space data set.

In a second aspect of the present disclosure, a system for generating a magnetic resonance (MR) image is provided. The system may include a storage configured to store instructions, and at least one processor configured to execute the instructions. When executing the instructions, the at least one processor causes the system to perform one or more of the following operations. A first calibration region may be determined in a calibration data set including a plurality of data points. The calibration data set may relate to a receiver coil. A first relationship between the first data point and the first plurality of data points including the first data point in the first calibration region may be constructed. A synthesizing filter may be generated based on the first relationship. The synthesizing filter may be stored in electronic form as a data file. The synthesizing filter may be adapted for generating an image relating to the receiver coil. The first calibration region may include a matrix having a first plurality of data points. The first plurality of data points may include a first data point at the center of the first calibration region. The calibration data set may include a fully-acquired k-space data set that includes no unknown data points. In some embodiments, the calibration data set may be generated based on complete signals and/or undersampled signals. The first data point may be at the center of the first calibration region. The calibration region may be part of the calibration data set. The calibration region may have a size of n×m, wherein n or m may each represent an integer. The synthesizing filter may be a convolution kernel. In some embodiments, the convolution kernel may be of the same size as the first calibration region.

In some embodiments, the system may be further configured to determine a second calibration region in the calibration data set based on the first calibration region (the second calibration region includes a matrix having a second plurality of data points, the second plurality of data points including a second data point at the center of the second calibration region), construct a second relationship between the second data point and the second plurality of data points including the second data point in the second calibration region, and generate the synthesizing filter based on the second relationship. The second data point is at the center of the second calibration region. The second calibration region may have the same size as the first calibration region. In some embodiments, the second calibration region and the first calibration region may be in the same k-space lines.

In a third aspect of the present disclosure, a method for generating a magnetic resonance (MR) image is provided. The method may include one or more of the following operations. A first plurality of MR signals representing an undersampled data set may be acquired by a receiver coil. The first plurality of MR signals may include undersampled MR signals. The undersampled data set may include at least one unknown data point. A second plurality of MR signals representing a calibration data set comprising a plurality of data points may be acquired by the receiver coil. The second plurality of MR signals may include complete signals and/or undersampled signals. The calibration data set may be without unknown data points. A first relationship between a first data point at the center of a first calibration region of the calibration data set and the data points in the first calibration region may be constructed. The data points in the first calibration region comprises the data point at the center of the first calibration region. The construction of the first relationship between a first data point at the center of a first calibration region of the calibration data set and the data points in the first calibration region may include one or more of the following operations. The first calibration region in the calibration data set may be determined, the first calibration region including a matrix having a first plurality of data points, the first plurality of data points may include a first data point at the center of the first calibration region. The first relationship between the first data point and the first plurality of data points including the first data point in the first calibration region may be constructed. A synthesizing filter may be generated based on the first relationship. The synthesizing filter may be a convolution kernel.

In some embodiments, the convolution kernel may be of the same size as the first calibration region. The synthesizing filter may be applied to the undersampled data set to generate a complete data set. The undersampled data set may include a plurality of filtering regions. The synthesizing filter may be applied to the plurality of filtering regions in the undersampled data set. A filtering region may be part of the undersampled k-space data set. In some embodiments, a filtering region may include at least one unknown data point. In some embodiments, the size of a filtering region may be the same as the size of the synthesizing filter. In some embodiments, the filtering region may have a size of n×m, wherein n or m may each represent an integer number. An image may be generated based on the complete data set.

In some embodiments, the method may further include one or more of the following operations. A second calibration region in the calibration data set may be determined based on the first calibration region. The second calibration region may have the same size as the first calibration region. In some embodiments, the second calibration region and the first calibration region may be in the same k-space lines. The second calibration region may include a matrix having a second plurality of data points, the second plurality of data points including a second data point at the center of the second calibration region. A second relationship between the second data point and the second plurality of data points including the second data point in the second calibration region may be constructed. The synthesizing filter may be generated based on the second relationship.

In some embodiments, the calibration data set includes MRI data.

In some embodiments, the second calibration region and the first calibration region may partly overlap with each other.

In some embodiments, the second data point and the first data point may be filled in a k-space line.

In some embodiments, the calibration data set may be without unknown data points.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a block diagram of an MRI system according to some embodiments of the present disclosure;

FIG. 1-B is a block diagram of a computing device according to some embodiments of the present disclosure;

FIG. 9-A is a schematic illustration of a k-space data set;

FIG. 9-B is a schematic illustration of a calibration data set;

FIG. 9-C is a schematic illustration of a first filtering region;

FIG. 9-D is a schematic illustration of a second filtering region; and

DETAILED DESCRIPTION

Figure 2:
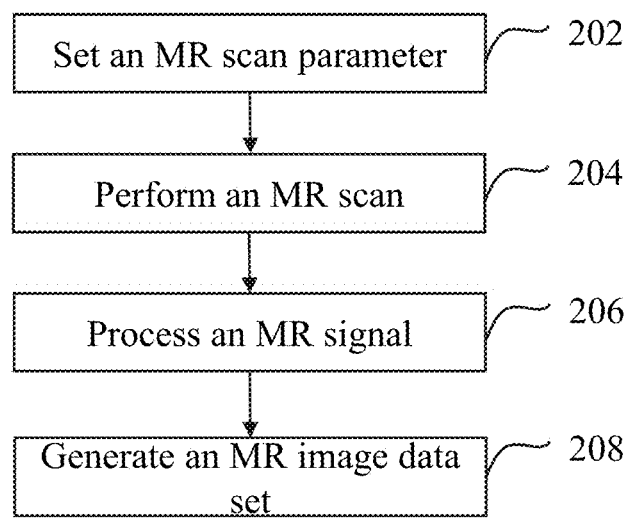
FIG. 2 is a flowchart of an MR scan according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

FIG. 1-A is a block diagram of a magnetic resonance imaging (MM) system 100 according to some embodiments of the present disclosure. As illustrated, the MM system 100 may include an MM scanner 110, a controller 120, a processing module 130, etc. The MM scanner 110 may include a magnet module 111 and a radio frequency (RF) module 112. In some embodiments, the MRI scanner 110 may perform a scan on a subject or a region of the subject. The subject may be, for example, a human body or other animal body. For example, the subject may be a patient. The region of the subject may include part of the subject. For example, the region of the subject may include a tissue of the patient. The tissue may include, for example, lung, prostate, breast, colon, rectum, bladder, ovary, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the scan may be a pre-scan for calibrating an imaging scan. In some embodiments, the scan may be an imaging scan for generating an image.

The magnet module 111 may include a main magnet field generator and/or a gradient magnet field generator (not shown in FIG. 1-A). The main magnet field generator may create a static magnetic field BO during a scan. The main magnet may be of various types including, for example, a permanent magnet, a superconducting electromagnet, a resistive electromagnet, etc.

The gradient magnet field generator may generate magnet field gradients on the main magnet field BO in a certain direction, for example, X, Y, and/or Z directions. As used herein, the X, Y and Z direction may represent X, Y and Z axis in a coordinate system. Merely by way of example, the X axis and the Z axis may be in a horizontal plane, the X axis and the Y axis may be in a vertical plane, the Z axis may be along the rotational axis of the gantry. In some embodiments, the X axis, the Y axis, and the Z axis may be specified by the gradient magnet field generator (i.e., gradient coils in the gradient magnet field generator). The gradient magnet field may encode and/or readout the spatial information of the subject (or a region of the subject) located within the MM scanner 110.

In some embodiments, the magnet module 111 may generate magnet field gradients in a set of directions during a scan. Merely by way of example, the magnet module 111 may generate a first magnet field gradient in a first direction, a second magnet field gradient in a second direction, and a third magnet field gradient in a third direction. In some embodiments, the first, second, and third direction, may be along the X axis, the Y axis, and the Z axis, respectively. In some embodiments, the magnet field gradients along the X axis, the Y axis, and/or the Z axis may correspond to different encoding/readout directions in the k-space (e.g., the direction of the kx axis, the direction of the ky axis, the direction of the kz axis, or any other direction).

The function, size, type, geometry, position, amount, and/or magnitude of the magnet module 111 and/or of the RF module 112 may be determined or changed according to one or more specific conditions. Merely by way of example, the magnet module 111 and the radio frequency (RF) module 112 may be designed to surround a subject (or a region of the subject) to form a tunnel type MRI scanner 110 (i.e. a close-bore MRI scanner 110), or an open MM scanner 110 (i.e. an open-bore MM scanner 110). In some embodiments, the RF module 112 may be classified as transmitter coils and/or receiver coils. These RF coils may transmit RF signals to, or receive RF signals from the subject (or a region of the subject). Merely by way of example, the transmitter coils may transmit RF energy to the subject (or a region of the subject) to induce electrical signals in the region of interest. As another example, the receiver coils may pick up RF electromagnetic radiation produced by nuclear relaxation inside the subject (or a region of the subject).

In some embodiments, according to the difference in function and/or size, the RF coils may be classified as volume coils and local coils. In some embodiments, the volume coils may include body coils, birdcage coils, transverse electromagnetic coils, saddle coils, etc. In some embodiments of the present disclosure, the local coils may include solenoid coils, saddle coils, flexible coils, surface coils, etc.

The surface coil may be a coil placed directly over the subject (or a region of the subject). In some embodiments, the surface coil may be a receiver coil configured to receive signals produced by nuclear relaxation inside the subject (or a region of the subject). Merely by way of example, the surface coil may receive a plurality of MR signals during a pre-scan and/or an imaging scan. For example, the surface coil may be placed directly over a region of interest (ROI) of the subject, providing improved signal to noise ratios (SNR) by limiting the spatial extent of the reception. In some embodiments, the surface coil may be a loop of a conducting material. Merely by way of example, the surface coil may be a copper tubing. In some embodiments, the loop may form various shapes. Merely by way of example, the loop may be bent to conform with the body part to be examined. In some embodiments, the radio frequency (RF) module 112 may include one or more surface coils. Merely by way of example, the radio frequency (RF) module 112 may include a plurality of surface coils.

The body coil may be a coil that surrounds the subject (or a region of the subject). Merely by way of example, the body coil may surround the head or the knee of a patient being examined. In some embodiments, the body coil may be a receiver coil configured to receive signals produced by nuclear relaxation inside the subject (or a region of the subject), and/or a transmitter coil configured to transmit RF energy to the subject (or the region of the subject). Merely by way of example, the body coil may receive a plurality of MR signals during a pre-scan and/or an imaging scan.

In some embodiments, the radio frequency (RF) module 112 may include one or more receiver coils. The coils may include surface coils and/or body coils. Merely by way of example, the radio frequency (RF) module 112 may include a first receiver coil and a second receiver coil. Both the first receiver coil and the second receiver coil may be surface coils. As another example, both the first receiver coil and the second receiver coil may be body coils. In some embodiments, the radio frequency (RF) module 112 may include one or more body coils. Merely by way of example, the radio frequency (RF) module 112 may include a body coil surrounding the patient being examined.

The controller 120 may control the magnet module 111 and/or the RF module 112 of the MRI scanner 110, the image processing engine 130, etc. Merely by way of example, the controller 120 may control the magnet field gradients in the X direction, the Y direction, and the Z direction. In some embodiments, the controller 120 may receive information from, or send information to the MM scanner 110, the processing 130, etc. According to some embodiments, the controller 120 may receive commands from, for example, a user, and adjust the magnet module 111 and/or RF module 112 to take images of the subject (or a region of the subject) according to the received commands.

In some embodiments, the controller 120 may include an input/output device to receive commands input from the user (for example, a doctor, a nurse, an imaging specialist, etc.). Merely by way of example, the input/output device may include a video display, a track ball, a mice, a keyboard, a microphone, a touch-sensitive display, a transducer card reader, a magnetic or paper tape reader, a tablet, a stylus, a voice or handwriting recognizer, a biometrics reader, a computer, or any combination thereof.

In some embodiments, the controller 120 may communicate with the image processing engine 130 for exchanging information relating to the operation of the MRI scanner 110 or other parts of the MRI system 100. Control logic (software) and data may be stored in a storage device. The storage device may be a main memory or a secondary storage. The main memory may include a random access memory (RAM), a read only memory (ROM), etc. The secondary storage may include, for example, a hard disk drive and/or a removable storage drive, representing a floppy disk drive, a magnetic tape drive, a compact disk drive, etc. The removable storage drive may read from and/or write data to a removable storage unit in a certain manner. In some embodiments, the storage device may be implemented in the MM system 100. For example, the storage device may be implemented in the controller 120 and/or the image processing engine 130. In some embodiments, the storage device may be an external storage connected to the MM system 100. In some embodiments of the present disclosure, the controller 120 may be implemented on a computing device 150 as illustrated in FIG. 1-B and the description thereof, via its hardware, software program, firmware, or a combination thereof.

The image processing engine 130 may process different kinds of information received from different modules. In some embodiments, the image processing engine 130 may communicate with or connect to the MRI scanner 110, the controller 120, etc. To better illustrate the present disclosure, several examples are given below, but the examples do not limit the scope of the present disclosure. For example, in some embodiments, the image processing engine 130 may process MR signals received from the RF module 112 (for example, the surface coil(s) and/or the body coil(s)) and generate one or more MR data sets (for example, k-space data sets, or image data sets) based on these signals. Merely by way of example, the MR signals may be filled into a k-space to generate a k-space data set. In some embodiments, these signals may be received by a plurality of receiver coils. The signals received by a same receiver coil may be filled into a plurality of k-space lines of a same k-space. In some embodiments, a k-space line may be in the form of a data set filled with data points. Merely by way of example, the receiver coils may include a first receiver coil and a second receiver coil. The k-space of the first receiver coil may be a first k-space, the k-space of the second receiver coil may be a second k-space.

Merely by way of example, the first receiver coil may receive a signal A and a signal B; the signal A and the signal B may be filled into a first k-space line and a second k-space line of a first k-space, respectively. In some embodiments, the signal B may be received after the signal A. In some embodiments, the second k-space line may be adjacent to the first k-space line. In some embodiments, the signal A and/or the signal B may be undersampled signals. In some embodiments, the undersampled signals may be signals not fully acquired. Consequently, the first k-space line and the second k-space line of the first k-space may constitute an undersampled k-space data set of the first k-space. In some embodiments, an undersampled k-space data set may be a k-space data set including one or more unknown data points. In some embodiments, the first coil may further receive a signal C and a signal D, the signal C and the signal D may be complete signals. In some embodiments, the signal D may be received after the signal C. In some embodiments, the complete signals may be fully acquired signals. In some embodiments, the signal C and the signal D may be filled into a third k-space line and a fourth k-space line of the first k-space. In some embodiments, the third k-space line may be adjacent to the fourth k-space line. In some embodiments, the third K-space line may be next to the second k-space line. In some embodiments, a plurality of k-space lines may be between the second the k-space line and the third k-space line.

In some embodiments, a calibration data set may be selected from the k-space. In some embodiments, the calibration data set may include a fully-acquired k-space data set that includes no unknown data points. For instance, a portion of the first k-space line and a portion of the second k-space line may constitute a locally complete k-space data set of the first k-space, and a calibration data set. As another example, the third k-space line and the fourth k-space line, or a portion thereof, may constitute a calibration data set. As a further example, a portion of the first k-space line and a portion of the second k-space line, along with a portion of the third k-space line and a portion the fourth k-space line, may constitute a locally complete k-space data set of the first k-space, and a calibration data set. As still a further example, a portion of the second k-space line and a portion of the third k-space line may constitute a locally complete k-space data set of the first k-space, and a calibration data set.

The calibration data set may be used to generate information related to a parameter (for example, the coil sensitivity) relating to the receiver coil (for example, the first coil) that have received the calibration data set. In some embodiments, a synthesizing filter may be generated based on the calibration data set. The synthesizing filter may provide calibration information relating to the receiver coil for calibrating the undersampled data set that correspond to the signals received by the receiver coil.

The image processing engine 130 may generate a complete k-space data set based on the undersampled k-space data set and the synthesizing filter. The complete k-space data set may include the calibration data set and a filled-in undesampled k-space data set. In some embodiments, the unknown data points in the originally undersampled k-space data set may be determined to generate the filled-in undersampled k-space data set. Further, in some embodiments, the image processing engine 130 may generate an image data set based on the complete k-space data set.

The image processing engine 130 may generate a data set. The data set may include a candidate data set and/or a reference data set. In some embodiments, the image processing engine 130 may generate the candidate data set based on signals acquired during the pre-scan and/or the imaging scan. The candidate data set may include a first candidate data set and a second candidate data set. Merely by way of example, the image processing engine 130 may generate the first candidate data set based on signals acquired by the surface coil during the pre-scan. As another example, the image processing engine 130 may generate the second candidate data set based on signals acquired by the surface coil during the imaging scan. In some embodiments, the image processing engine 130 may generate the reference data set based on MR signals acquired during the pre-scan and/or the imaging scan. The reference data set may include a first reference data set and a second reference data set. Merely by way of example, the image processing engine 130 may generate the first reference data set based on signals acquired by the body coil during the pre-scan. As another example, the image processing engine 130 may generate the second reference data set based on signals acquired by the body coil during the imaging scan.

In some embodiments, the candidate data set may include a candidate k-space data set and/or a candidate image data set. Merely by way of example, the first candidate data set may include a first candidate k-space data set and/or a first candidate image data set. As another example, the second candidate data set may include a second candidate k-space data set and/or a second candidate image data set. The reference data set may include a k-space reference data set and/or a reference image data set. Merely by way of example, the first reference data set may include a first reference k-space data set and/or a first reference image data set. As another example, the second reference data set may include a second reference k-space data set and/or a second reference image data set. In some embodiments, the image processing engine 130 may generate a candidate k-space data set. The candidate k-space data set may be a surface coil k-space data set. The candidate k-space data set may be an MR k-space data set generated based on signals acquired by one or more surface coils. In some embodiments, the image processing engine 130 may generate a reference k-space data set for the candidate k-space data set. In some embodiments, the reference k-space data set may be a body coil k-space data set. The body coil k-space data set may be an MR k-space data set generated from signals acquired by one or more body coils.

In some embodiments, the image processing engine 130 may generate a candidate image data set. The candidate image data set may be a surface coil image data set. The surface coil image data set may be an MR image data set generated based on signals acquired by one or more surface coils during a pre-scan or an imaging scan. Merely by way of example, the surface coil may receive a first plurality of signals during the pre-scan, based on which the first candidate image data set may be generated. The first plurality of signals may correspond to a pre-scan region of the subject being examined. Merely by way of example, the first plurality of signals may correspond to the subject (for example, the patient).

In some embodiments, the image processing engine 130 may generate a reference image data set for the candidate image data set. In some embodiments, the reference image data set may be a body coil image data set. The body coil image data set may be an MR image data set generated from signals acquired by one or more body coils during a pre-scan or an imaging scan. Merely by way of example, the body coil may receive a second plurality of MR signals during the pre-scan, based on which the reference image data set may be generated. The second plurality of signals may correspond to the pre-scan region of the subject being examined. Further, in some embodiments, the surface coil may receive a third plurality of MR signals during the imaging scan, based on which the second candidate image data set may be generated. The third plurality of signals may correspond to a scan region of the subject being examined. The scan region of the subject may be located within the pre-scan region of the subject. In some embodiments, the body coil may receive a fourth plurality of MR signals during the imaging scan, based on which the second reference image data set may be generated. The fourth plurality signals may correspond to the scan region of the subject being examined.

In some embodiments, a corrector may be generated based on the candidate image data set and the reference image data set. For example, a corrector may be generated based on the first candidate image data set and the first reference image data set. As another example, the corrector may be generated based on the second candidate image data set and the second reference image data set. The generated corrector may be applied to the first candidate image data set and/or the second candidate image data set. In some embodiments, the generated corrector may be utilized to correct a data set that was used to generate the corrector. Merely by way of example, the second candidate image data set may be corrected by a corrector that was generated based on the second candidate image data set and the second reference image data set. In some embodiments, the generated corrector may be utilized to correct a data set (for example, a third image data set) that was not used to generate the corrector. The third image data set may be generated based on signals acquired by one or more surface coils. Merely by way of example, the second candidate image data set may be corrected by a corrector that was generated based on the first candidate image data set and the first reference image data set.

In some embodiments, the candidate data set (for example, the first candidate data set or the second candidate data set) may have a higher SNR compared to the reference data set (for example, the first reference data set or the second reference data set). In some embodiments, the candidate data set may have a higher intensity inhomogeneity compared to the reference data set. A corrector may be utilized to correct the intensity inhomogeneity in the candidate data set (for example, the first candidate data set or the second candidate data set). In some embodiments, the corrector may be generated based on the candidate data set and the reference data set. Merely by way of example, the corrector may be generated based on the second candidate image data set and the second reference image data set. As another example, the generated corrector may be applied to the first candidate image data set and/or the second candidate image data set. The corrector may be in an image domain. In some embodiments, the image processing engine 130 may generate a corrected image data set based on the corrector. Merely by way of example, the image processing engine 130 may generate the corrected image data set by applying the corrector to the candidate data set (for example, the first candidate data set or the second candidate data set). In some embodiments, the generated corrector may be utilized to correct a data set that was used to generate the corrector. Merely by way of example, the second candidate data set may be corrected by a corrector that was generated based on the second candidate data set and the second reference data set. In some embodiments, the generated corrector may be utilized to correct a data set (for example, the third image data set) that was not used to generate the corrector. The third image data set may be generated based on signals acquired by surface coil(s). Merely by way of example, the second candidate image data set may be corrected by a corrector that was generated based on the first candidate data set and the first reference data set. The corrected image data set may be an intensity weighted image data set. In some embodiments, the corrected image data set may be displayed or otherwise output. In some embodiments, the image processing engine 130 may process data input by the user or an operator and transform the data into specific commands, and supply the commands to the controller 120. In some embodiments of the present disclosure, the image processing engine 130 may be implemented on a computing device 150 as illustrated in FIG. 1-B and the description thereof, via its hardware, software program, firmware, or a combination thereof.

It should be noted that the above description of the MM system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MM system 100 may be varied or changed according to specific implementation scenarios. Merely by way of example, some other components may be added into the MM system 100, such as a patient positioning module, a gradient amplifier module, and other devices or modules. Note that the MRI system 100 may be a traditional or a single-modality medical system, or a multi-modality system including, e.g., a positron emission tomography-magnetic resonance imaging (PET-MM) system, a remote medical MRI system, and others, etc. However, those variations and modifications do not depart from the scope of the present disclosure.

FIG. 1-B illustrates an exemplary architecture of a computing device 150 according to some embodiments of the present disclosure. In some embodiments, the controller 120, the image processing engine 130, or a portion thereof, or a combination thereof, may be implemented on the computing device 150 via its hardware, software program, firmware, or a combination thereof.

The computing device 150 may include an internal communication bus 151, a central processing unit (CPU) 152, an I/O interface 156, a communication port 155, and one or more memory devices. The internal communication bus 151 may transmit data between the components (152 through 157) of the computing device 150. For example, the MM data from the disk 157 may be transmitted through internal communication bus 151 to the CUP 152 to generate an image data set.

The central processing unit (CPU) 152 may execute computer instructions. The computer instructions may relate to routines, programs, objects, components, data structures, procedures, modules, etc. In some embodiments, the CPU 152 may process the data or information received from the MM scanner 110, the controller 120, or any other component of the MM system 100. In some embodiments, CPU 152 may include one or more processors. The processors may include a microcontroller, a microprocessor, a reduced instruction set computer (MSC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced MSC machine (ARM), a programmable logic device (PLD), any circuit or processor capable of executing one or more functions, or the like, or any combinations thereof. For example, the processors may include a microcontroller to process the MRI data received from the MM scanner 110 for image reconstruction.

The one or more memory devices may store the data or information received from the MM scanner 110. In some embodiments, the memory devices may include a disk 157, a random access memory 154 (RAM), a read-only memory 153 (ROM), or the like, or any combination thereof. The disk 157 may be implemented by, for example, a magnetic disk, an optical disk, a floppy disk, an optical disk, or a zip disk, etc. The RAM 154 may be implemented by, for example, a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM 153 may be implemented by, for example, a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the memory devices may store one or more programs and/or instructions to perform exemplary methods described in the present disclosure. For example, the ROM 153 may store a program or an algorithm for reconstructing an MR image based on the MR data.

The computing device 150 may include one or more COM ports 155 connected to a network to furnish data communications. The communication ports (COM ports) 155 may transmit information to or receive information from MM scanner 110 via a network. In some embodiments, communication ports 155 may include a wired port (e.g., a Universal Serial Bus (USB), a High Definition Multimedia Interface (HDMI), a wireless port (such as a Bluetooth port, an infrared interface, and a WiFi port), or the like, or any combination thereof.

The I/O interface 156 may support information input or output between the computing device 150 and one or more peripherals. In some embodiments, the peripherals may include a terminal, a keyboard, a touch screen, a cursor control device, a remote controller, or the like, or any combination thereof. The terminal may include, for example, a mobile device (e.g., a smart phone, a smart watch, a laptop computer, or the like), a personal computer, or the like, or any combination thereof. For example, the terminal may be implemented by a computer 158, which may be a general purpose computer or a specially designed computer. The cursor control device may include a mouse, a trackball, or cursor direction keys to communicate direction information and command selections to, for example, the image processing engine 130 or control cursor movement on a display device.

The information input and/or output via I/O interface 156 may include programs, software, algorithms, data, text, number, images, voices, or the like, or any combination thereof. For example, the user may input some initial parameters or conditions to initiate an MM data processing. In some embodiments, the information input via I/O interface 156 may be input via a keyboard, a touch screen, a voice sensor, a motion sensor, a brain monitoring system, or any other devices.

Those skilled in the art will recognize that the present teachings are amenable to a variety of modifications and/or enhancements. For example, although the implementation of various components described herein may be embodied in a hardware device, it may also be implemented as a software only solution, e.g., an installation on an existing server. For example, the image processing engine 130 and/or the controller 120 as disclosed herein may be implemented as a firmware, a software, or a combination thereof.

FIG. 2 is a flowchart of an MR scan according to some embodiments of the present disclosure. In 202, an MR parameter may be set. The MR parameter may relate to an MR scanning, a protocol selection, a signal acquisition, a data processing, a data storage, a data calibration, an image generation, or the like, or any combination thereof. Merely by way of example, the MR parameter may include an image contrast and/or ratio, the region of interest (ROI), slice thickness, an imaging type (e.g., T1 weighted imaging, T2 weighted imaging, proton density weighted imaging, etc.), a spin echo type (spin echo, fast spin echo (FSE), fast recovery FSE, single shot FSE, gradient recalled echo, fast imaging with stead-state procession, and etc.), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. In some embodiments, the MR parameter may be set in the controller 120. In some embodiments, the MR parameter may be set via the computing device 150 through a user interface.

In 204, an MR scan may be performed by, for example, the MRI scanner 110. In some embodiments, an MR parameter including a pulse sequence may be sent to the MRI scanner 110 to generate RF excitation pulses and magnetic field gradients during the MR scan. The pulse sequence may be, for example, a spin echo (SE) sequence, a fast spin echo (FSE) sequence, an ultrashort echo-time (UTE) sequence, a gradient echo (GRE) sequence, etc. Merely by way of example, a radial 3D UTE sequence may be provide to the MM scanner 110. In some embodiments, the pulse sequence may be sent to the MM scanner 110 in a form of a timing diagram. In some embodiments, an MR signal may be acquired during the MR scan. In some embodiments, the acquired MR signal may be an analog signal.

In 206, the MR signal acquired during the MR scan may be processed by, for example, the image processing engine 130. The MR signal acquired during the MR scan may be detected or acquired by the surface coil and/or the body coil.

In some embodiments, various signal processing methods may be applied to process the acquired signal. Merely by way of example, the signal processing methods may include analog-to-digital conversion, linear fitting, 2D Fourier transform (2D FT), fast Fourier transform (FFT), interpolation algorithm, regridding, or the like, or any combination thereof. In some embodiments, the acquired signal may be converted to a set of discrete data. Furthermore, the discrete data may be processed to fill into the k-space to generate a k-space data set. Merely by way of example, the MR signals acquired by a surface coil may be filled into a k-space of the surface coil. As another example, the MR signals acquired by a body coil may be filled into a k-space of the body coil.

The MR signals acquired by the surface coil may be filled into the k-space of the surface coil to generate a candidate k-space data set. In some embodiments, the MR signals acquired by the surface coil may be acquired during a pre-scan and/or an imaging scan. The MR signals acquired by the surface coil during the pre-scan may include the first plurality of MR signals. The MR signals acquired by the surface coil during the imaging scan may include the third plurality of MR signals. Merely by way of example, the first plurality of MR signals may be filled into the k-space of the surface coil to generate the first candidate k-space data set. As another example, the third plurality of MR signals may be filled into the k-space of the surface coil to generate the second candidate k-space data set. The MR signal acquired by the body coil may be filled into the k-space of the body coil to generate a reference k-space data set. In some embodiments, the MR signals acquired by the body coil may be acquired during a pre-scan and/or an imaging scan. The MR signals acquired by the body coil during the pre-scan may include the second plurality of MR signals. The MR signals acquired by the body coil during the imaging scan may include the fourth plurality of MR signals. Merely by way of example, the second plurality of MR signals may be filled into the k-space of the body coil to generate the first reference k-space data set. As another example, the fourth plurality of MR signals may be filled into the k-space of the body coil to generate the second reference k-space data set.

In some embodiments, a corrector may be generated based on the candidate k-space data set and the reference k-space data set. Merely by way of example, the corrector may be generated based on the first candidate k-space data set and the first reference k-space data set. As another example, the corrector may be generated based on the second candidate k-space data set and the second reference k-space data set. Further, in some embodiments, the generator corrector may be configured to correct the candidate k-space data set (for example, the first candidate k-space data set and/or the second candidate k-space data set). In some embodiments, the acquired signal may include undersampled signals and complete signals. In some embodiments, the undersampled signals and the complete signals may be received by a same coil. In some embodiments, the undersampled signals may be filled into a k-space to generate the undersampled k-space data set. In some embodiments, the complete signals may be filled into the k-space to generate the calibration data set. In some embodiments, a synthesizing filter may be generated based on the calibration data set. The calibration data set may be applied to the undersampled k-space data set to generate a complete k-space data set.

In 208, an MR image data set may be generated based on the processed signal. In some embodiments, the image processing engine 130 may be configured to generate the MR image. In some embodiments, the MR image may be generated based on the complete k-space data set. In some embodiments, the image data set may be generated by repeating 202 through 206 for a certain number of times. In some embodiments, the certain number of times may be determined by the MRI system 100 or provided by the user (e.g., a doctor). In some embodiments, the generated image data set may be the candidate image data set, and/or the reference image data set. The candidate image data set may be generated based on the MR signals acquired by the surface coil. The reference image data set may be generated based on the MR signals acquired by the body coil.

In some embodiments, the generated image data set may be a T1-weighted image data set, a T2-weighted image data set, a PD (proton density)-weighted image data set, an FLAIR (fluid attenuated inversion recovery) image data set, an intensity weighted image data set, or the like. Merely by way of example, the intensity weighted image data set may be generated based on the candidate image data set and the reference image data set. Specifically, the candidate image data set and the reference image data set may be generated based on the processed signals. The corrector configured to correct the intensity inhomogeneity in the candidate image data set may be generated based on the candidate image data set and the reference image data set. Further, the intensity weighted image data set may be generated by correcting the candidate image data set with the corrector. In some embodiments, the intensity weighted image data set may be further processed to generate a report. The intensity weighted image data set and/or the generated report may be output to a related device (e.g., to be printed, to be displayed, or the like).

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 204 and 206 for storing the acquired MR signal.

Figure 3:
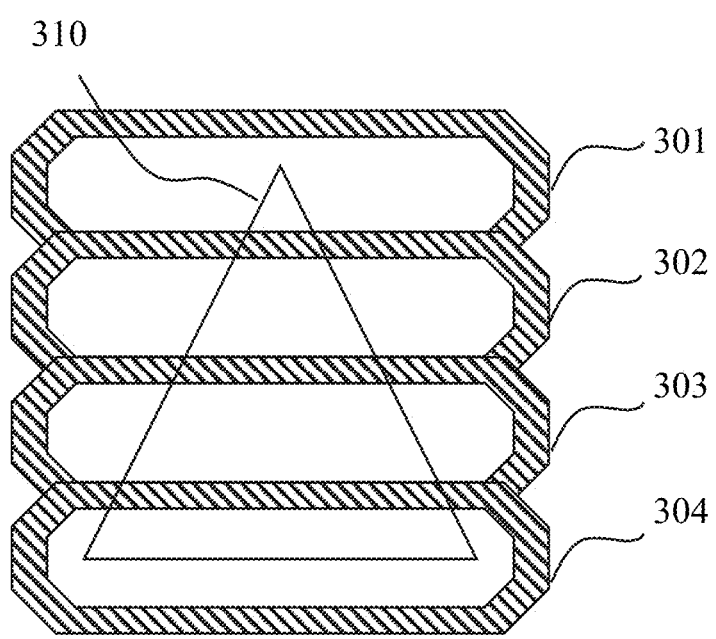
FIG. 3 is a schematic illustration of an RF module.

FIG. 3 is a schematic illustration of the RF module 112. The RF module 112 may include a first receiver coil 301, a second receiver coil 302, a third receiver coil 303, and a fourth receiver coil 304. In some embodiments, the receiver coils may be surface coils or body coils. The first receiver coil 301, the second receiver coil 302, the third receiver coil 303, and the fourth receiver coil 304 may receive MR signals emitted from the subject 310. In some embodiments, the receiver coils may receive the MR signals in parallel. The subject 310 may be, for example, a human body or other animal body, or part of the human body or animal body. For example, the subject may be a patient. As another example, the subject may be a tissue of the patient. The tissue may include but not limited to, for example, lung, prostate, breast, colon, rectum, bladder, ovary, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the signals received by the first receiver coil 301, the second receiver coil 302, the third receiver coil 303, and the fourth receiver coil 304 may be filled into a first k-space, a second k-space, a third k-space, and a fourth k-pace, respectively, to generate a first image, a second image, a third image, and a fourth image. In some embodiments, the first image, the second image, the third image, and the fourth image may be combined to generate an MR image data set relating to the subject.

Figure 4:
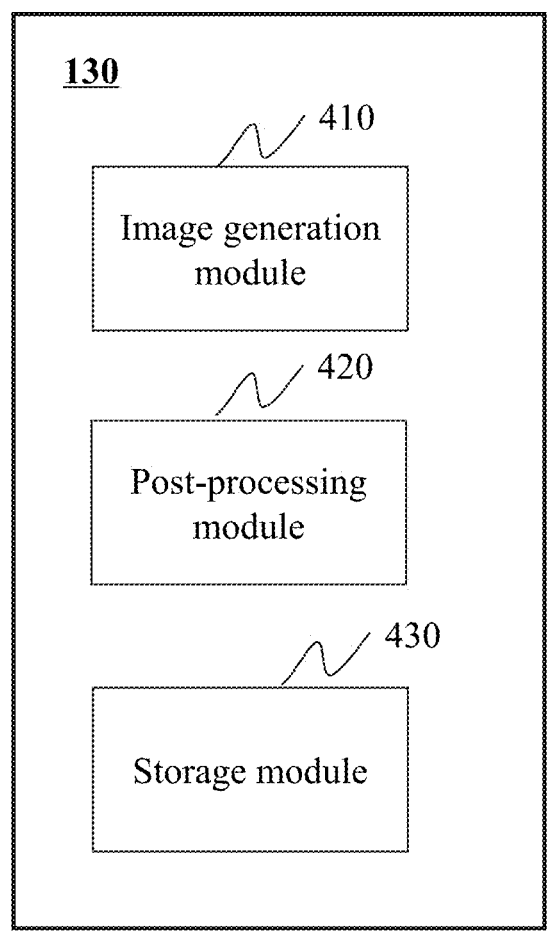
FIG. 4 is a block diagram of the image processing engine according to some embodiments of the present disclosure.

FIG. 4 is a block diagram of the image processing engine 130 according to some embodiments of the present disclosure. The image processing engine 130 as illustrated in FIG. 1-A may process information before, during, or after an imaging procedure. It is understood that the construction of the image processing engine 130 may have some other variations, and that FIG. 4 is provided for illustration purposes. The image processing engine 130 may include a CPU. The CPU may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As illustrated in FIG. 4, the image processing engine 130 may include an image generation module 410, a post-processing module 420, and a storage module 430.

The image generation module 410 may be configured to generate an image data set based on the MR signals acquired during the MR scan. In some embodiments, the MR signals may be acquired by a plurality of receiver coils (for example, the first receiver coil 301 and the second receiver coil 302). The plurality of receiver coils may include surface coils and body coils. The MR signals received by a same receiver coil (for example, the first receiver coil 301 or the second receiver coil 302) may be filled into a plurality of k-space lines of a same k-space (for example, the first k-space or the second k-space) by the image generation module 410. In some embodiments, the image generation module 410 may fill the MR signals into the k-space according to a Cartesian pattern. In some embodiments, the image generation module 410 may fill the MR signals into the k-space according to a non-Cartesian pattern. Exemplary non-Cartesian pattern may include but not limited to radial and spiral pattern. In some embodiments, a non-Cartesian pattern may be gridded to a Cartesian coordinates. In some embodiments, the MR signals may include undersampled signals, the k-space lines filled with the undersampled signals may include an undersampled k-space data set. In some embodiments, the k-space lines filled with the undersampled signals may include a locally complete data set or a calibration data set. In some embodiments, the MR signals may include complete signals, all or portion of the k-space lines filled with the complete signals may constitute a calibration data set.

In some embodiments, the image generation module 410 may generate the synthesizing filter based on the calibration data set. The image generation module 410 may further apply the generated synthesizing filter to the undersampled k-space data set to generate a complete k-space data set. Further, in some embodiments, the image generation module 410 may generate an image data set based on the complete k-space data set.

In some embodiments, the image generation module 410 may communicate with or connect to the post-processing module 420, the storage module 430, the controller 120, the MRI scanner 110, etc. In some embodiments, the image generation module 410 may calculate different kinds of information from the MM scanner 110, or received from the controller 120, etc. The information from the MM scanner 110 may be a plurality of MR signals of a subject. The information from the controller 120 may include information about the MRI scanner 110, the magnet module 111, a patient position (e.g., within an MRI system 100), the RF module 112, or the like, or any combination thereof. In some embodiments, the information may be a patient position, the main and/or gradient magnet intensity, the radio frequency phase and/or amplitude, and so on. The information from the controller 120 may include information from the user and/or other external resource. Exemplary information from the user may include parameters regarding image contrast and/or ratio, a subject of interest (e.g., the type of tissue to be imaged, etc.), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. The image generation module 410 may process the data such as magnetic resonance (MR) signals acquired from the subject of interest and reconstruct them into an MR image. In some embodiments, the image generation module 410 may convert analog MR signals to digital MR signals. In some embodiments, one or more parameters may be set before or during the conversion, e.g., voltage, current, rate, sampling frequency, or the like, or a combination thereof. The converted MR signals may be stored in the storage module 430. In some embodiments, the image generation module 410 may spatially decode an MR signal that has been spatially encoded by the magnetic field(s). The intensity or magnitude of the signal, and other properties such as a phase number, a relaxation time (T1 or T2), magnetization transfer, or the like, may be ascertained. The image generation module 410 may employ different kinds of image reconstruction techniques for the image reconstruction procedure. Exemplary image reconstruction techniques may include but not limited to Fourier reconstruction, constrained image reconstruction, regularized image reconstruction in parallel MRI, or the like, or a variation thereof, or any combination thereof.

The post-processing module 420 may post-process the image received from the image generation module 410 and/or the storage module 430. The post-processing may include displaying and/or operating on the image received from the image generation module 410 and/or the storage module 430. The displaying processing may include but not limited to sub-screen displaying, contrast displaying, amplification displaying, or the like, or any combination thereof. The operation on the image may include but not limited to correcting, cutting, magnifying, window adjusting, rotating, batch processing, or the like, or any combination thereof. In some embodiments, the post-processing module 420 may correct an error, or reduce or remove an artifact in the image data set received from the image generation module 410. Merely by way of example, the post-processing module 420 may reduce or remove an intensity inhomogeneity in the image. In some embodiments, the post-processing module 420 may extract specific details about the subject being examined. In some embodiments, the specific details about the subject being examined may enhance interpretation of the diagnostic result.

The storage module 430 may store the information that may be used by the image generation module 410 and/or the post-processing module 420. The information may include but not limited to programs, software, algorithms, data, text, number, images and some other information. These examples are provided here for illustration purposes, and not intended to limit the scope of the present disclosure. Algorithms stored in the storage module 430 may include but not limited to recursion, a bisection method, an exhaustive search (or brute-force search), a greedy algorithm, a divide and conquer algorithm, a dynamic programming method, an iterative method, a branch-and-bound algorithm, a back-tracking algorithm, or the like, or any combination thereof. In some embodiments, the storage module 430 may store MR signals transmitted by the image generation module 410. In some embodiments, the storage module 430 may store the undersampled k-space data set, the calibration data set and/or the generated MR image data sets received from the image generation module 410. In some embodiments, the storage module 430 may store the post-processed MR image transmitted by the post-processing module 420.

It should be noted that the above description of the image processing engine 130 is merely provided for the purposes of illustration, and not intended to limit the scope of the present disclosure. For persons having ordinary skills in the art, multiple variations or modifications may be made under the teachings of the present disclosure. For example, the assembly and/or function of processing unit may be varied or changed. In some embodiments, the image generation module 410 and the post-processing module 420 may share one storage module 430. While in some embodiments, the image generation module 410 and the post-processing module 420 may have their own storage blocks, respectively. However, those variations and modifications do not depart from the scope of the present disclosure.

Figure 5:
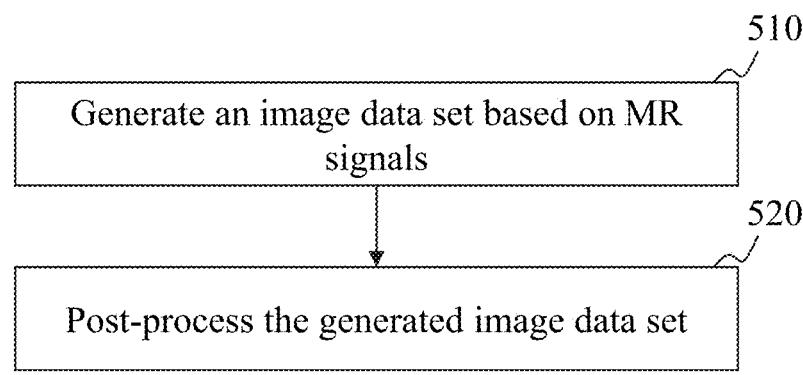
FIG. 5 is a flowchart of a process for generating an MR image according to some embodiments of the present disclosure.

FIG. 5 is a flowchart of a process for generating an MR image according to some embodiments of the present disclosure.

In 510, an image may be generated based on MR signals. The image generation module 410 may generate the image data set. The MR signals may be acquired by a plurality of receiver coils (for example, the first receiver coil 301, the second receiver coil 302, etc.). In some embodiments, the MR signals may include undersampled MR signals and complete MR signals. The MR signals may be filled into the k-space. In some embodiments, the MR signals acquired by a same receiver coil (for example, the first receiver coil 301 or the second receiver coil 302) may be filled into the same k-space (for example, a first k-space or a second k-space). Merely by way of example, undersampled signals by a same receiver coil may be filled into the k-space to generate the undersampled k-space data set, and complete MR signals may be filled into the k-space, at least a portion of which may constitute a calibration data set. In some embodiments, a synthesizing filter may be generated based on the calibration data set, and be applied to the undersampled k-space data set to generate a complete k-space data set. The image may be generated based on the complete k-space data set.

In some embodiments, different kinds of image reconstruction techniques may be utilized to generate the image data set based on the complete k-space data set. Exemplary image reconstruction techniques may include but not limited to Fourier reconstruction, constrained image reconstruction, regularized image reconstruction in parallel MRI, or the like, or a variation thereof, or any combination thereof.

In 520, the image generated may be post-processed. The post-processing module 420 may perform the post-processing. In some embodiments, the post-processing may include displaying and/or operating on the image generated. The displaying processing may include but not limited to sub-screen displaying, contrast displaying, amplification displaying, or the like, or any combination thereof. The operation on the image may include but not limited to correcting, cutting, magnifying, window adjusting, rotating, batch processing, or the like, or any combination thereof. In some embodiments, an error or artifact in the image (for example, intensity inhomogeneity) may be corrected, reduced, or removed. In some embodiments, specific details about the subject being examined may be extracted through post-processing. In some embodiments, the specific details about the subject being examined may facilitate interpretation of the diagnostic result.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 510 and 520 for storing the generated image.

Figure 6:
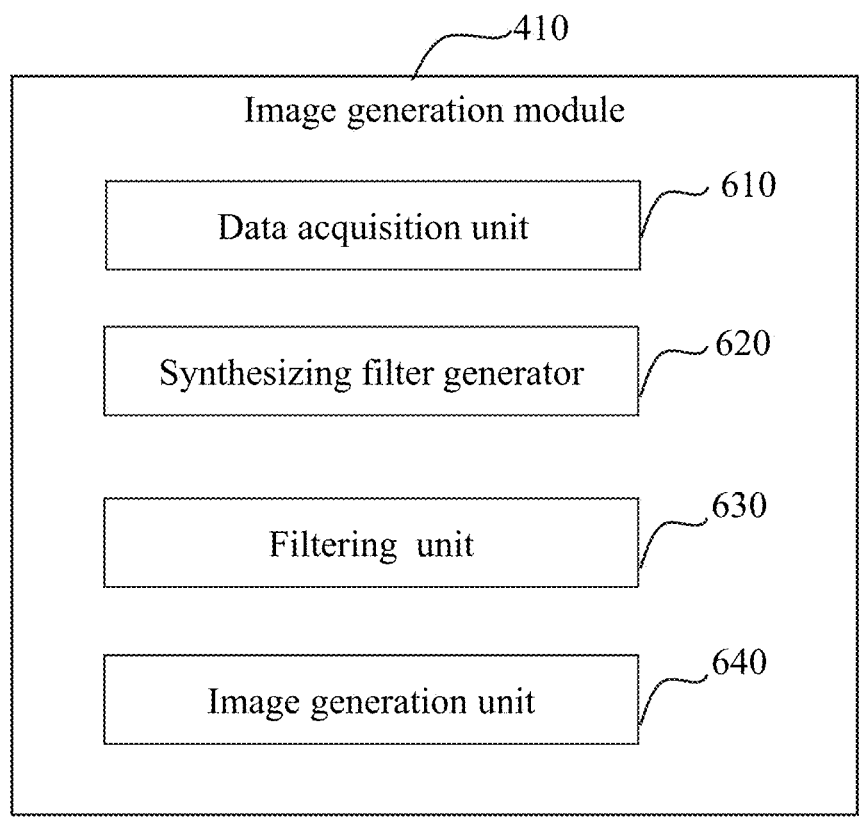
FIG. 6 is a block diagram of an image generation module according to some embodiments of the present disclosure.

FIG. 6 is a block diagram of an image generation module 410 according to some embodiments of the present disclosure. As illustrated in FIG. 6, the image generation module 410 may include a data acquisition unit 610, a synthesizing filter generator 620, a filtering unit 630, and an image generation unit 640.

The data acquisition unit 610 may communicate with the MRI scanner 110, a storage device, the controller 120, the synthesizing filter generator 620, and/or the filtering unit 630. Merely by way of example, the data acquisition unit 610 may acquire MR signals from the MRI scanner 110. In some embodiments, the MR signals may be acquired by a plurality of different receiver coils (for example, the first receiver coil 301, the second receiver coil 302, etc.). In some embodiments, the MR signals may include undersampled signals and complete signals. Merely by way of example, the first receiver coil 301 may receive a plurality of under-sampled signals (for example, the signal A and the signal B as exemplified above) and a plurality of complete signals (for example, the signal C and the signal D as exemplified above).

The synthesizing filter generator 620 may generate the synthesizing filter. In some embodiments, the synthesizing filter may provide calibration information relating to the receiver coil. Merely by way of example, the synthesizing filter may include a convolutional kernel. In some embodiments, the synthesizing filter generator 620 may communicate with the data acquisition unit 610, the filtering unit 630, and/or the storage module 430. Merely by way of example, the synthesizing filter generator 620 may receive the undersampled MR signals from the data acquisition unit 610. In some embodiments, the synthesizing filter generator 620 may fill the undersampled MR signals into a corresponding k-space (for example, the k-space corresponding to the receiver coil having received the undersampled MR signals) to generate the undersampled k-space data set. In some embodiments, the undersampled k-space data set may include a portion that is locally complete, the portion having no unknown data points. In some embodiments, the locally complete portion of the undersampled k-space data set may include a calibration data set. As another example, the synthesizing filter generator 620 may receive the complete MR signals from the data acquisition unit 610. The synthesizing filter generator 620 may fill the complete MR signals into the corresponding k-space. Merely by way of example, the first receiver coil 301 may acquire the complete signals. The synthesizing filter generator 620 may fill the complete signals into a plurality of k-space lines of the first k-space. In some embodiment, all or a portion of the plurality of k-space lines may constitute a calibration data set.

Figure 10:
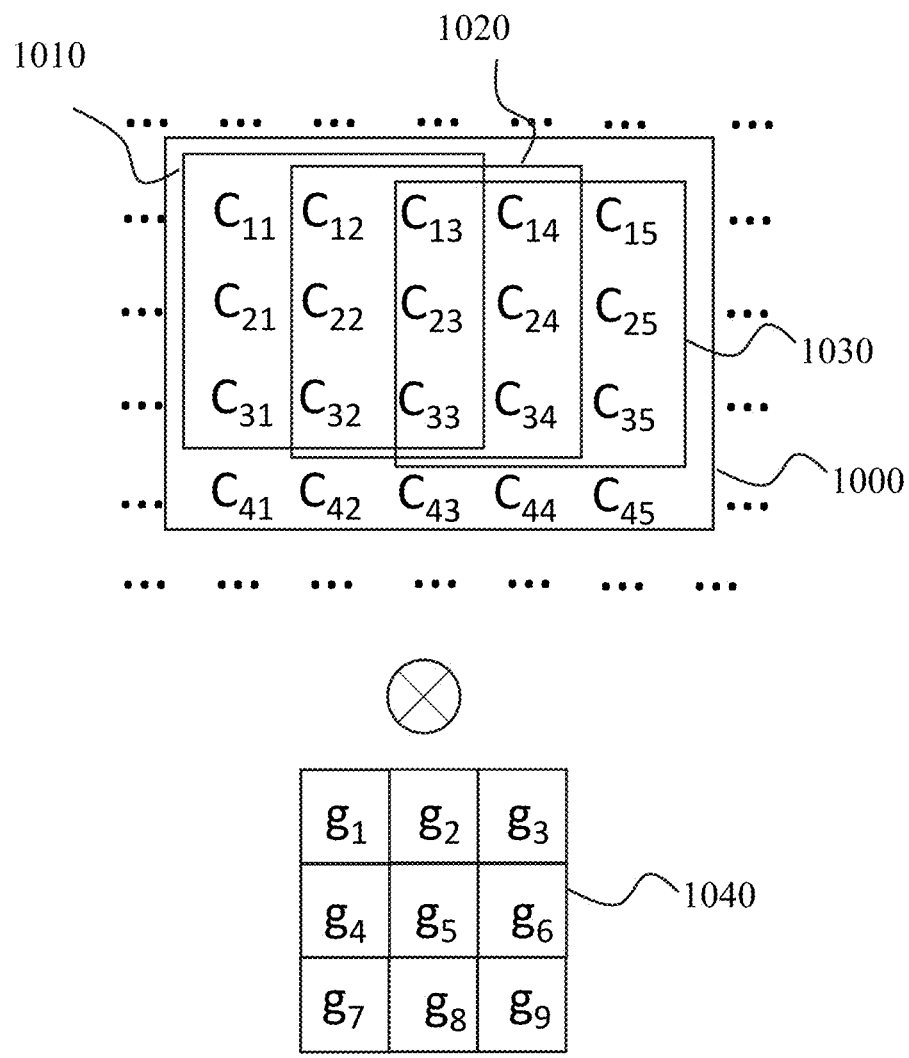
FIG. 10 is a schematic illustration of the generation of a synthesizing filter.

A calibration data set may include a plurality of data points. In some embodiments, the calibration data set does not include unknown data points. In some embodiments, the synthesizing filter generator 620 may generate a synthesizing filter based on the calibration data set. In some embodiments, the synthesizing filter generator 620 may determine one or more calibration regions in the calibration data set. Merely by way of example, the calibration region may include a first calibration region and a second calibration region. A calibration region may be part of the calibration data set. The calibration region may include a matrix having a plurality of data points. Merely by way of example, as illustrated in FIG. 10, the first calibration region 1010 may be a matrix having a plurality of data points. As another example, the second calibration region 1020 may be a matrix having a plurality of data points. As another example, the third calibration region 1030 may be a matrix having a plurality of data points. The calibration region may have a size of n×m, wherein n or m may represent an integer number. In some embodiments, the size of the calibration region may be the same as the size of the synthesizing filter. In some embodiments, the synthesizing filter generator 620 may generate a synthesizing filter based on one calibration region (for example, the first calibration region).

In some embodiments, the calibration region (for example, the first calibration region) may include a data point at the center of the calibration region. Merely by way of example, as illustrated in FIG. 10, the first calibration region 1010 may be a matrix, $C_{22}$ may be the data point at the center of the first calibration region 1010. As another example, the second calibration region 1020 may be a matrix, $C_{23}$ may be the data point at the center of the second calibration region 1020. As another example, the third calibration region 1030 may be a matrix, $C_{24}$ may be the data point at the center of the third calibration region 1030. The synthesizing filter generator 620 may construct a relationship between the data point at the center of the calibration region and the data points in the calibration region. Merely by way of example, the synthesizing filter may be a convolution kernel generated based on the data point at the center of the calibration region and the data points in the calibration region. In some embodiments, the synthesizing filter may be arranged in a Cartesian sampling pattern or non-Cartesian sampling pattern. In some embodiments, the synthesizing filter generator 620 may generate the synthesizing filter based on a relationship. In some embodiments, the synthesizing filter may generate the synthesizing filter based on a plurality of calibration regions (for example, the first calibration region and the second calibration region). Merely by way of example, the synthesizing filter may generate a first relationship and a second relationship based on the first calibration region and the second calibration region, respectively, and generate the synthesizing filter based on the first relationship and the second relationship. In some embodiments, the synthesizing filter may send the generated synthesizing filter to the filtering unit 630.

The filtering unit 630 may utilize the synthesizing filter. The filtering unit 630 may communicate with the MRI scanner 110, the storage module 430, the data acquisition unit 610, and/or the synthesizing filter generator 620. Merely by way of example, the filtering unit 630 may receive the synthesizing filter and the undersampled k-space data set from the synthesizing filter generator 620. As another example, the filtering unit 630 may receive the undersampled MR signals from the data acquisition unit 610 and/or the MRI scanner 110. In some embodiments, the filtering unit 630 may apply the synthesizing filter to the undersampled k-space data set. In some embodiments, the filtering unit 630 may fill the undersampled MR signals into the k-space to generate the undersampled k-space data set, and based on the synthesizing filter, to generate the filled-in undersampled k-space data-set.

In some embodiments, the filtering unit 630 may determine a plurality of filtering regions. A filtering region may be part of the undersampled k-space data set. In some embodiments, a filtering region may include at least one unknown data point. In some embodiments, the size of the filtering region may be the same as the size of the synthesizing filter. In some embodiments, the filtering region may have a size of n×m, wherein n or m may represent an integer number.

In some embodiments, the filtering unit 630 may apply the synthesizing filter on a filtering region to generate an equation with at least one unknown data point. Merely by way of example, the filtering region may include a data point at the center of the filtering region. The filtering unit 630 may construct a relationship between the data point at the center of the filtering region and the data points in the filtering region. The relationship may be in the form of an equation. The data point at the center of the filtering region and the data points in the filtering region may include at least one unknown data point. Merely by way of example, the data point at the center of the filtering region may be unknown. As another example, a data point other than the data point at the center may be unknown.

In some embodiments, the filtering unit 630 may apply the synthesizing filter to the plurality of filtering regions to generate a plurality of equations with respect to a plurality of unknown data points. In some embodiments, the plurality of equations with respect to the plurality of unknown data points may be solved simultaneously. In some embodiments, the plurality of equations may be solved by iteration, until a termination condition is satisfied. Merely by way of example, the termination condition may relate to a number of iterations. The termination condition may be satisfied when a certain number of iterations have been performed. As another example, the termination condition may be satisfied when the results converge (e.g., the difference of the results of two consecutive iterations falls below a threshold). In some embodiments, the termination condition may be provided by a user (for example, a doctor, a nurse, an imaging specialist, etc.), or by the MRI system 100. Merely by way of example, the number of iterations to be performed may be set by the user. As another example, the threshold value may be provided by the user. As a further example, the termination condition may be set based on a default setting of the MM system 100. Merely by way of example, the plurality of filtering regions may include a first filtering region, and/or a second filtering region. The first filtering region may include a first unknown data point, and a second unknown data point. The second filtering region may include a third unknown data point and a fourth data point. The filtering unit 630 may apply the synthesizing filter to the first filtering region and the second filtering region to generate a first equation and a second equation, respectively. The filtering unit 630 may apply the synthesizing filter to the first filtering region and the second filtering region sequentially or simultaneously. The first equation may be with respect to the first unknown data point and the second unknown data point, and the second equation may be with respect to the third unknown data point and the fourth unknown data point. In some embodiments, at least one of the third unknown data point and the fourth unknown data point may be the same as at least one of the first unknown data point and the second unknown data point, resulting the coupling of the first equation and the second equation. Consequently, the filtering unit 630 may solve the first equation and the second equation simultaneously. In some embodiments, a plurality of coupled equations may further be utilized associated the coupled first equation and the second equation to determine the first unknown data point and the second unknown data point, the third unknown data point and the fourth unknown data point. Merely by way of example, as illustrated in FIG. 9-A through FIG. 9-D, 910 may represent the calibration data set, 920 and 930 may represent the first filtering region and the second filtering region in the undersampled k-space data set. The calibration data set 910 may be fully acquired, including a plurality of data points 911. The first filtering region 920 and the second filtering region may be partly filled. The first filtering region may include five known data points: 921, 922, 923, 924, and 925, four unknown data points: 926, 927, 928, and 929. The second filtering region may include four known data points: 922, 924, 925, and 933, five unknown data points: 926, 928, 929, 931, and 932.

The synthesizing filter may be applied to the first filtering region to generate the first equation involving the unknown data points, 926, 927, 928, and 929. The synthesizing filter may be applied to the second filtering region to generate the second equation involving the unknown data points, 926, 928, 929, 931, and 932.

The first equation and the second equation may include the same unknown data points, 926, 928, and 929. In some embodiments, the first equation and the second equation may be coupled. In some embodiments, a third filtering region and a fourth filtering region may be determined, and a third equation and a fourth equation may be constructed accordingly. The plurality of equation determined based on the plurality of filtering regions may be combined, and be solved simultaneously to determine all the unknown data points in the calibration regions.

In some embodiments, the filtering unit 630 may generate the filled-in undersampled k-space data set by determining the unknown data points in the undersampled k-space data set. In some embodiments, the filled-in undersampled k-space data set and the calibration data set may constitute a complete k-space data set.

The image generation unit 640 may generate an image data set based on the complete k-space data set. In some embodiments, the image generation unit 640 may communicate with the filtering unit 630, the MRI scanner 110, the storage module 430, and/or the data acquisition unit 610. Merely by way of example, the image generation unit 640 may acquire the complete k-space data set from the filtering unit 630, and generate the image data set based on the complete k-space data set. The image generation unit 640 may employ different kinds of image reconstruction techniques for the image reconstruction procedure. Exemplary image reconstruction techniques may include but not limited to Fourier reconstruction, constrained image reconstruction, regularized image reconstruction in parallel MM, or the like, or a variation thereof, or any combination thereof.

It should be noted that the above description of the image generation module 410 is merely provided for the purposes of illustration, and not intended to limit the scope of the present disclosure. For persons having ordinary skills in the art, multiple variations and modifications may be made under the teachings of the present disclosure. For example, the assembly and/or function of the image generation module 410 may be varied or changed according to specific implementation scenarios. Merely by way of example, the data acquisition unit 610 may be configured to fill the MR signals into the k-space to generate the k-space data set.

Figure 7:
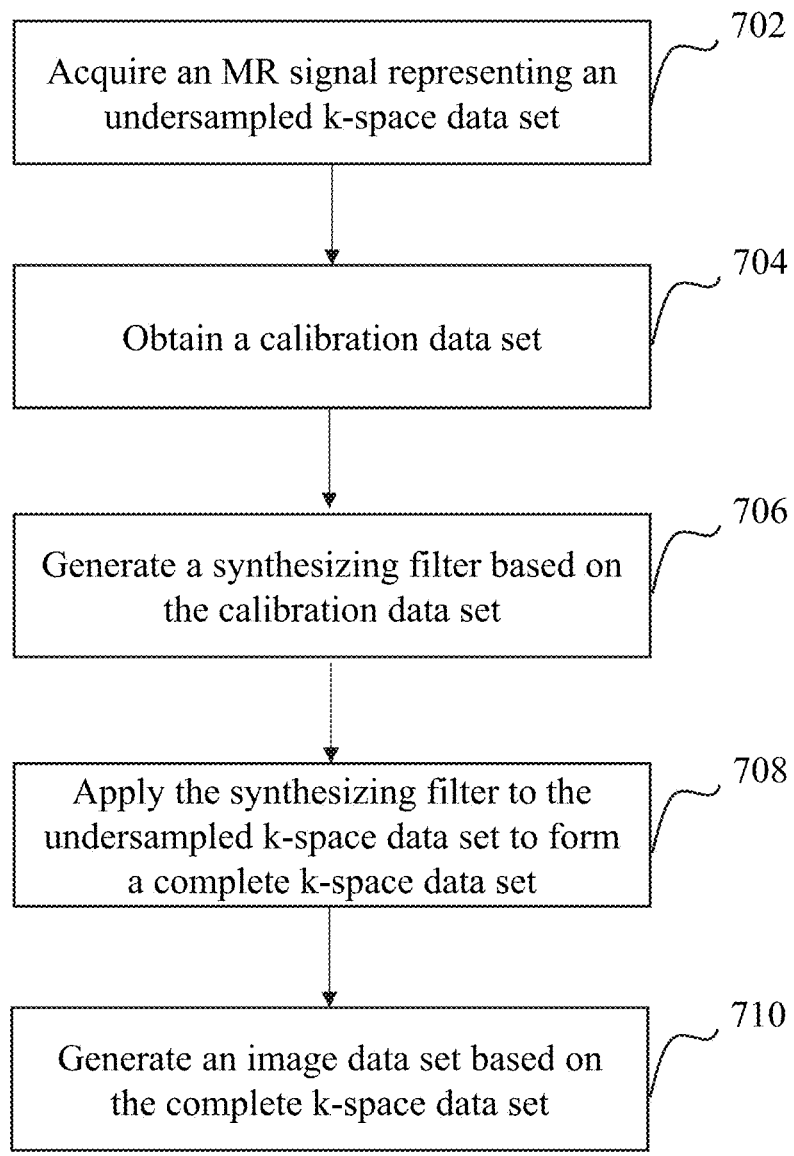
FIG. 7 is a flowchart of a process for generating an MR image according to some embodiments of the present disclosure.

FIG. 7 is a flowchart of a process for generating an MR image according to some embodiments of the present disclosure.

In 702, an undersampled MR signal representing an undersampled k-space data set may be acquired. In some embodiments, the MR signal may be acquired by the data acquisition unit 610. In some embodiments, the undersampled signal may be acquired by a receiver coil (for example, the first receiver coil 301), and be filled into a k-space line of a k-space (for example, the first k-space corresponding to the first receiver coil 301). In some embodiments, the k-space line filled with the undersampled signal may include an undersampled k-space data set. In some embodiments, a plurality of undersampled MR signals may be acquired by the first receiver coil 301, and be filled into a plurality of k-space lines of the first k-space. In some embodiments, the MR signals may be filled into the plurality of k-space lines of the first k-space according to a Cartesian pattern or a non-Cartesian pattern. Exemplary non-Cartesian pattern may include but not limited to a radial pattern, a spiral pattern, etc. In some embodiments, a non-Cartesian pattern may be gridded to a Cartesian coordinate system. The plurality of k-space lines filled with the undersampled MR signals may include an undersampled k-space data set. In some embodiments, the undersampled k-space data set may include a portion that is locally complete, the portion having no unknown data points.

In 704, a calibration data set may be obtained. In some embodiments, the calibration data set may include a plurality of data points. In some embodiments, the plurality of data points may be fully acquired. In other words, the calibration data set does not include an unknown data point. The calibration data set may be acquired by the data acquisition unit 610. In some embodiments, the calibration data set may be generated based on complete MR signals. The complete signals may be received by the receiver coil (for example, the first receiver coil 301). In some embodiments, the calibration data set may be generated by filling one or more complete MR signals into a plurality of k-space lines of the first k-space. In some embodiment, all or a portion of the plurality of k-space lines may constitute the calibration data set. In some embodiments, the calibration data set may be extracted from the undersampled k-space data set obtained in 702. For instance, the calibration data set may be extracted from a portion of the undersampled k-space data set, the portion being locally complete and having no unknown data points.

In 706, a synthesizing filter may be generated based on the calibration data set. The synthesizing filter may be generated by the synthesizing filter generator 620. In some embodiments, the synthesizing filter may be in the form of a data set. Merely by way of example, the synthesizing filter may be a convolution kernel. In some embodiments, the synthesizing filter may be arranged in a Cartesian sampling pattern or non-Cartesian sampling pattern. In some embodiments, the calibration data set may include one or more calibration regions. A calibration region may be part of the calibration data set. The calibration region may include a matrix including a plurality of data points. The calibration region may have a size of n×m, wherein n or m may represent an integer number. In some embodiments, the size of the calibration region may be the same as the size of the synthesizing filter. In some embodiments, the synthesizing filter may be generated based on one or more calibration regions. In some embodiments, the calibration region may include a data point at the center of the calibration region. The relationship may be constructed between the data point at the center of the calibration region and the data points in the calibration region, the synthesizing filter may be generated based on the relationship. In some embodiments, the synthesizing filter may generate the synthesizing filter based on a plurality of calibration regions (for example, the first calibration region and the second calibration region). Merely by way of example, the synthesizing filter may construct a first relationship and a second relationship based on the first calibration region and the second calibration region, respectively, and generate the synthesizing filter based on the first relationship and the second relationship. In some embodiments, the first relationship and the second relationship may be generated sequentially. In some embodiments, the synthesizing filter may have the same size as the calibration region.

In 708, the synthesizing filter may be applied to the undersampled k-space data set to form a complete k-space data set. The filtering unit 630 may apply the synthesizing filter to the undersampled k-space data set. In some embodiments, the undersampled k-space data set may include a plurality of filtering region, the synthesizing may be applied to the plurality of filtering regions. In some embodiments, the filtering region may have the same size as the synthesizing filter. In some embodiments, the filtering region may include at least one unknown data point. The synthesizing filter may be applied to the plurality of filtering regions sequentially or simultaneously. Merely by way of example, the undersampled k-space data set may include the first filtering region and the second filtering region. The first filtering region may include the first unknown data point, and the second unknown data point. The second filtering region may include the third unknown data point and the fourth unknown data point. The synthesizing filter may be applied to the first filtering region and the second filtering region to generate the first equation and the second equation, respectively. The first equation may be with respect to the first unknown data point and the second unknown data point, and the second equation may be with respect to the third unknown data point and the fourth unknown data point. In some embodiments, at least one of the third unknown data point and the fourth unknown data point may be the same as at least one of the first unknown data point and the second unknown data point, resulting the coupling of the first equation and the second equation. Consequently, the first equation and the second equation may be solved simultaneously. In some embodiments, a plurality of coupled equations may further be utilized associated the coupled first equation and the second equation, all of which may be solved simultaneously, to determine the first unknown data point and the second unknown data point (or the third unknown data point and the fourth unknown data point). In some embodiments, the filled-in undersampled k-space data set may be generated by determining the unknown data points in the undersampled k-space data set. In some embodiments, the filled-in undersampled k-space data set and the calibration data set may constitute the complete k-space data set.

In 710, an image data set may be generated based on the complete k-space data set. The image data set may be an MR image data set. In some embodiments, the image generation unit 640 may generate the image data set based on the complete k-space data set. In some embodiments, different kinds of image reconstruction techniques may be employed for the image reconstruction procedure. Exemplary image reconstruction techniques may include Fourier reconstruction, constrained image reconstruction, regularized image reconstruction in parallel MRI, or the like, or a variation thereof, or any combination thereof.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 706 and 708 for storing the synthesizing filter.

Figure 8:
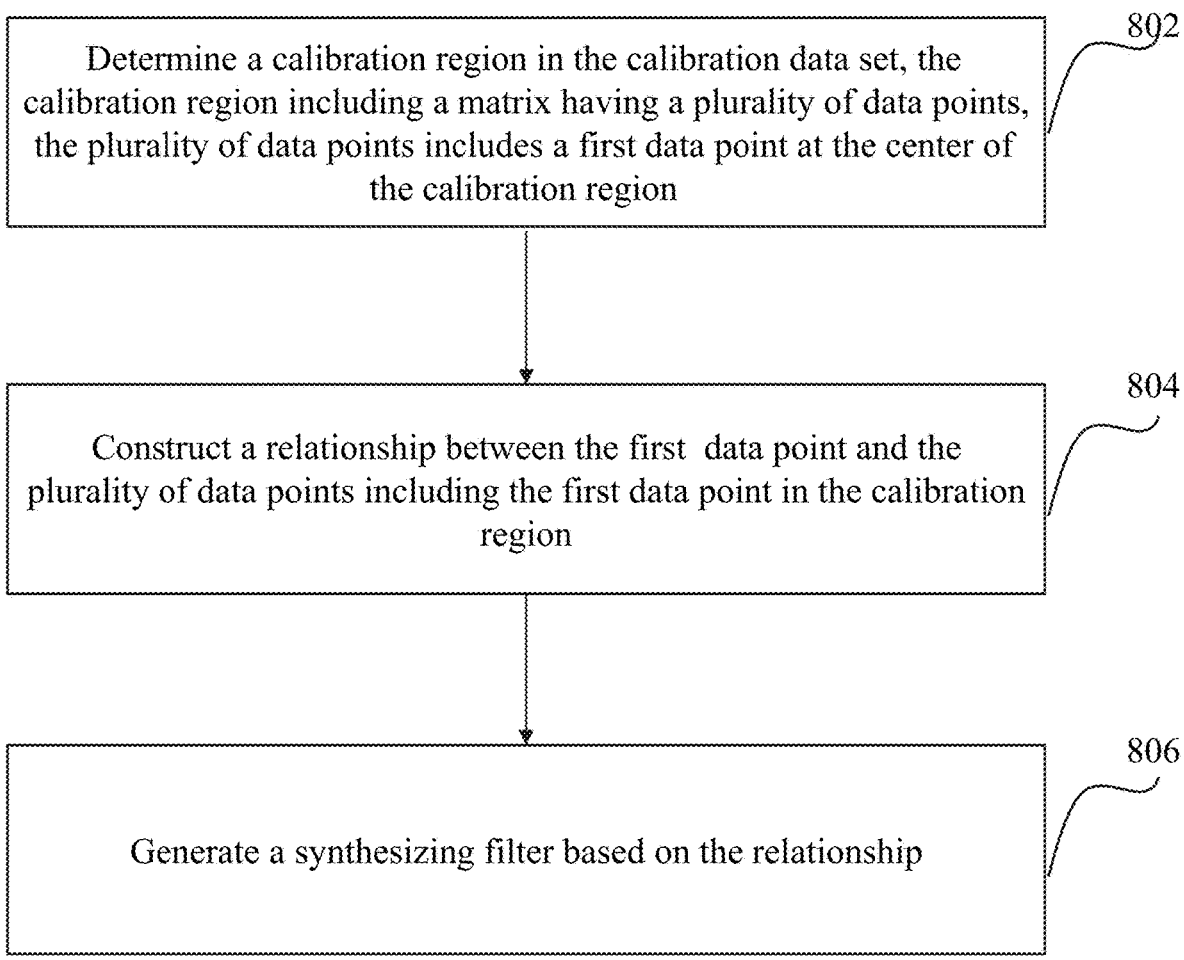
FIG. 8 is a flowchart of a process for generating an synthesizing filter according to some embodiments of the present disclosure.

FIG. 8 is a flowchart of a process for generating the synthesizing filter according to some embodiments of the present disclosure.

In 802, a calibration region in the calibration data set may be determined, the calibration region including a matrix having a plurality of data points. The plurality of data points may include a first data point at the center of the calibration region. In some embodiments, the synthesizing filter generator 620 may determine the calibration region in the calibration data set. The calibration region may be part of the calibration data set. The calibration region may include a matrix having a plurality of data points. Exemplary calibration region may be illustrated in FIG. 10 and the description thereof. As illustrated in FIG. 10, the calibration data set 1000 may include a first calibration region 1010, a second calibration region 1020, and a third calibration region 1030. In some embodiments, the calibration region may have a size of n×m, wherein n or m may represent an integer number. In some embodiments, the size of the calibration region may be the same as the size of the synthesizing filter. In some embodiments, a plurality of calibration regions may be determined in the calibration data set. See, for example, FIG. 9-A and FIG. 9-B, and the description thereof. Merely by way of example, the calibration data set may include a first calibration region and a second calibration region. The second calibration region may have the same size as the first calibration region. In some embodiments, the second calibration region and the first calibration region may be in the same k-space lines. In some embodiments, the first calibration region and the second calibration region may partly overlap with each other. The plurality of data points may include a first data point at the center of the calibration region. Merely by way of example, as illustrated in FIG. 10, $C_{22}$, $C_{23}$, and $C_{24}$ may be the data points at the centers of the first calibration region 1010, the second calibration region 1020, and the third calibration region 1030, respectively.

In 804, a relationship between the first data point at the center of the calibration region and the plurality of data points including the first data point in the calibration region may be constructed. In some embodiments, the calibration data set may include a plurality of calibration regions (for example, the first calibration region, the second calibration region, etc.). A plurality of relationships may be constructed based on the plurality of calibration regions. In some embodiments, a relationship may be constructed based on the center point of a calibration region and the plurality of data points in the same calibration region. For example, a first relationship between the center point of the first calibration region and the plurality of data points in the first calibration region may be constructed, in which the plurality of data points in the first calibration region may include the center point at the center of the first calibration region. A second relationship between the center point at the center of the second calibration region and the plurality of data points in the second calibration region may be constructed, in which the plurality of data points in the second calibration region may include the center point at the center of the second calibration region. In some embodiments, the synthesizing filter may be generated based on the first relationship and the second relationship. In some embodiments, the relationship may be generated by $$x=Hz. \qquad (1)$$

Equation (1) illustrates a relationship generated based on the data point at the center of a calibration region and the plurality of data points (including the data point at the center of the calibration region) in the calibration region. In Equation (1), x represents the data point at the center of the calibration region, z represents the transpose of [x, y], wherein y represents the data points in the calibration region other than x, and H is a convolution kernel. In some embodiments, H may be the synthesizing filter. In some embodiments, H may be a matrix. In some embodiments, the size of H may be the same as the size of the calibration region.

In some embodiments, H may be generated by $$H=[c1\, G, c2], \qquad (2)$$

in which G may be determined as $$x=Gy. \qquad (3)$$

In Equation (3), G is a convolution kernel. In some embodiments, G may be a convolution kernel generated based on a calibration data set. Merely by way of example, a plurality of coupled equations may be generated based on the calibration data set. The plurality of coupled equations may be solved using, for example, a least square technique, such as:

$$G=Y^{-1}X. \qquad (4)$$

in which X and Y are data matrices, representing a plurality of data points x and y; $Y^{-1}$ represents the pseudo-inverse of data matrix Y.

In some embodiments, G may be a matrix. The root mean square of one or more residuals of the Equation (4) may be denoted as $r_1$. The root mean square of the k-space noise may be denoted as $r_2$. $c_1$ may be a coefficient related to $r_1$ and $r_2$. $c_2$ may be a coefficient related to $r_1$ and $r_2$. In some embodiments, $c_1$ may be generated based on $r_1$ and $r_2$. In some embodiments, $c_1$ may be generated by $$c_1=r_2/(r_1+r_2). \qquad (5)$$

In some embodiments, $c_2$ may be generated by $$c_2=r_1/(r_1+r_2). \qquad (6)$$

In some embodiments, given that one of $c_1$ and $c_2$ is known, the other one may be generated based on the relationship illustrated in Equation (7):

$$c_1+c_2=1. \qquad (7)$$

In 806, a synthesizing filter may be generated based on one or more relationships. Merely by way of example, the synthesizing filter may be a convolution kernel generated based on the one or more relationships constructed in 804. As illustrated in 804, the synthesizing filter may be the convolution kernel H.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure.

FIG. 9-A is a schematic illustrations of the undersampled k-space data set including a portion 910 having a locally complete data set without unknown data points. FIG. 9-B is a schematic illustration of the calibration data set. FIG. 9-C is a schematic illustration of the first filtering region. FIG. 9-D is a schematic illustration of the second filtering region.

FIG. 10 is a schematic illustration of the generation of a synthesizing filter. The calibration data set 1000 may include a first calibration region 1010, a second calibration region 1020, and a third calibration region 1030. The data set 1040 may represent the convolution kernel. The data points in the first calibration region 1010, the second calibration region 1020, and the third calibration region 1030 may be known. As illustrated, the first calibration region 1010 may be a matrix including a plurality of data points. The second calibration region 1020 may be a matrix including a plurality of data point. The third calibration region 1030 may be a matrix including a plurality of data points. $C_{22}$, $C_{23}$, and $C_{24}$ may be the points at the centers of the first calibration region 1010, the second calibration region 1020, and the third calibration region 1030, respectively. A first relationship may be generated based on $C_{22}$ and the other data points in the first calibration region 1010. A second relationship may be generated based on $C_{23}$ and the other data points in the second calibration region 1020. A third relationship may be generated based on $C_{24}$ and the other data points in the third calibration region 1030. The first relationship may be illustrated as follows:

$$g_1c_{11}+g_2c_{12}+g_3c_{13}+g_4c_{21}+g_5c_{22}+g_6c_{23}+g_7c_{31}+g_8c_{32}+g_9c_{33}=C_{22}. \quad (8)$$

The second relationship may be illustrated as follows:

$$g_1c_{12}+g_2c_{13}+g_3c_{14}+g_4c_{22}+g_5c_{23}+g_6c_{24}+g_7c_{32}+g_8c_{33}+g_9c_{34}=C_{23}. \quad (9)$$

The third relationship may be illustrated as follows:

$$g_1c_{13}+g_2c_{14}+g_3c_{15}+g_4c_{23}+g_5c_{24}+g_6c_{25}+g_7c_{33}+g_8c_{34}+g_9c_{35}=C_{24}. \quad (10)$$

In some embodiments, Equation (8), Equation (9), and Equation (10) may be solved for determining the coefficients in the convolution kernel. In some embodiments, the number of the equations may be larger than the number of the coefficients in the convolution kernel. The equations may be solved using, for example, a least square technique.

It should be noted that the above description is merely provided for the purposes of illustration, and not intended to limit the scope of the present disclosure. The image producing procedures in the present disclosure may be effective in reducing, removing or eliminating other types of motion artifacts including, for example, the vascular pulsation, heart movement, and random motion of the subject being scanned, or the like, or any combination thereof. The image producing procedures in the present disclosure may be applied to whole body MR imaging, and the images produced may have more clear structural details.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method, implemented on at least one machine each of which has at least one processor and a storage, the method comprising:

acquiring, by a receiver coil, a plurality of magnetic resonance (MR) signals;

acquiring a calibration data set relating to the plurality of MR signals;

determining a first calibration region in the calibration data set, the first calibration region including a matrix having a first plurality of data points, the first plurality of data points including a first data point x at the center of the first calibration region;

constructing a first relationship between the first data point and the first plurality of data points including the first data point x and other data points y all around the first data point in the first calibration region;

generating a synthesizing filter H based on the first relationship in which H=[c1G, c2], wherein G is a convolution kernel determined by an equation: x=Gy, and c1 and c2 relate to coefficients r1 and r2, r1 being a root mean square of one or more residuals of the equation, and r2 being a root mean square of k-space noise of the plurality of MR signals; and storing, in the storage, the synthesizing filter in electronic form as a data file, wherein the synthesizing filter is adapted for determining an unknown data point in an undersampled k-space data set based on a signal acquired by the receiver coil.

2. The method of claim 1, further comprising:

determining a second calibration region in the calibration data set based on the first calibration region, the second calibration region including a matrix having a second plurality of data points, the second plurality of data points including a second data point at the center of the second calibration region;

constructing a second relationship between the second data point and the second plurality of data points including the second data point in the second calibration region; and generating the synthesizing filter based further on the second relationship.

3. The method of claim 2, wherein the second calibration region and the first calibration region partially overlap with each other.

4. The method of claim 2, wherein the second data point and the first data point are filled in a k-space line.

5. The method of claim 2, wherein the second calibration region and the first calibration region are of the same size.

6. The method of claim 1, wherein the synthesizing filter H includes a second convolutional kernel.

7. The method of claim 6, wherein the second convolutional kernel is of the same size as the first calibration region.

8. The method of claim 1, wherein the calibration data set is without unknown data points.

9. The method of claim 1, wherein the signal acquired by the receiver coil represents the undersampled k-space data set.

10. The method of claim 1, further comprising: applying the synthesizing filter on the undersampled k-space data set to form a complete k-space data set in which the unknown data point in the undersampled k-space data set is determined.

11. The method of claim 10, further comprising: generating an image data set based on the complete k-space data set.

12. A system comprising:

a storage configured to store instructions; and at least one processor configured to execute the instructions, wherein when executing the instructions, the at least one processor causes the system to perform operations including:

determining a first calibration region in a calibration data set relating to a receiver coil, the first calibration region having a matrix having a first plurality of data points, the first plurality of data points including a first data point x at the center of the first calibration region;

constructing a first relationship between the first data point and the first plurality of data points including the first data point x and other data points y all around the first data point in the first calibration region;

generating a synthesizing filter H based on the first relationship in which H=[c1G, c2], wherein
  G is a convolution kernel determined by an equation: x=Gy, and
  c1 and c2 relate to coefficients r1 and r2, r1 being a root mean square of one or more residuals of the equation, and r2 being a root mean square of k-space noise of the plurality of MR signals; and storing, in the storage, the synthesizing filter in electronic form as a data file,
wherein the synthesizing filter is adapted for determining an unknown data point in an undersampled k-space data set based on a signal acquired by the receiver coil.

13. The system of claim 12, wherein the calibration data set includes MRI data.

14. The system of claim 12, wherein the operations further including:
  determining a second calibration region in the calibration data set based on the first calibration region, the second calibration region including a matrix having a second plurality of data points, the second plurality of data points including a second data point at the center of the second calibration region;
  constructing a second relationship between the second data point and the second plurality of data points including the second data point in the second calibration region; and
  generating the synthesizing filter based further on the second relationship.

15. The system of claim 14, wherein the second calibration region and the first calibration region partly overlap with each other.

16. The system of claim 15, wherein the second data point and the first data point are filled in a k-space line.

17. The system of claim 12, wherein the synthesizing filter H includes a second convolutional kernel.

18. A method, implemented on at least one machine each of which has at least one processor and storage, the method comprising:
  acquiring, by a receiver coil, a first plurality of magnetic resonance (MR) signals representing an undersampled data set;
  acquiring, by the receiver coil, a second plurality of MR signals representing a calibration data set comprising a plurality of data points;
  constructing a first relationship between a first data point x at the center of a first calibration region of the calibration data set and a first plurality of data points in the first calibration region, wherein the first plurality of data points in the first calibration region includes the first data point x at the center of the first calibration region and other data points y all around the first data point;
  generating a synthesizing filter based on the first relationship in which H=[c1G, c2], wherein
    G is a convolution kernel determined by an equation: x=Gy, and
    c1 and c2 relate to coefficients r1 and r2, r1 being a root mean square of one or more residuals of the equation, and r2 being a root mean square of k-space noise of the plurality of MR signals;
  applying the synthesizing filter to the undersampled data set to generate a complete data set; and
  generating an image based on the complete data set.

19. The method of claim 18, wherein the constructing a first relationship between a first data point x at the center of a first calibration region of the calibration data set and a first plurality of data points in the first calibration region comprises:
  determining the first calibration region in the calibration data set, the first calibration region including a matrix having the first plurality of data points.

20. The method of claim 18, further comprising:
  determining a second calibration region in the calibration data set based on the first calibration region, the second calibration region including a matrix having a second plurality of data points, the second plurality of data points including a second data point at the center of the second calibration region;
  constructing a second relationship between the second data point and the second plurality of data points including the second data point in the second calibration region; and
  generating the synthesizing filter based further on the second relationship.

* * * * *